United States Patent
Neff

(10) Patent No.: US 10,424,031 B2
(45) Date of Patent: Sep. 24, 2019

(54) HEALTHCARE INFORMATION OPERATION SESSION AND DATA TRANSFER SYSTEM

(71) Applicant: Cerner Innovation, Inc., Kansas City, KS (US)

(72) Inventor: Robert A Neff, Villanova, PA (US)

(73) Assignee: CERNER INNOVATION, INC., Kansas City, KS (US)

(*) Notice: Subject to any disclaimer, the term of this patent is extended or adjusted under 35 U.S.C. 154(b) by 11 days.

(21) Appl. No.: 13/688,713

(22) Filed: Nov. 29, 2012

(65) Prior Publication Data
US 2014/0088983 A1 Mar. 27, 2014

Related U.S. Application Data

(60) Provisional application No. 61/706,300, filed on Sep. 27, 2012.

(51) Int. Cl.
*G06Q 50/20* (2012.01)
*G06Q 50/22* (2018.01)
*G06Q 10/10* (2012.01)
*G16H 10/60* (2018.01)

(52) U.S. Cl.
CPC .......... *G06Q 50/22* (2013.01); *G06Q 10/10* (2013.01); *G16H 10/60* (2018.01)

(58) Field of Classification Search
CPC .... G06F 19/322; G06F 19/3443; G06F 17/24; G06F 3/0484; G06F 9/4881; H04N 21/482; G06G 50/20
USPC .......................................................... 705/2
See application file for complete search history.

(56) References Cited

U.S. PATENT DOCUMENTS

| | | | |
|---|---|---|---|
| 5,996,365 A | 12/1999 | Tanaka | |
| 6,283,647 B1 | 9/2001 | Konishi et al. | |
| 7,278,579 B2 | 10/2007 | Loffredo et al. | |
| 7,703,682 B2 | 4/2010 | Kenney | |
| 7,708,198 B2 | 5/2010 | Gangi | |
| 7,712,658 B2 | 5/2010 | Gangi | |
| 7,967,190 B2 | 6/2011 | Hussey | |
| 2002/0132585 A1 | 9/2002 | Palermo et al. | |
| 2002/0161708 A1 | 10/2002 | Offer | |
| 2003/0144035 A1 | 7/2003 | Weinblatt et al. | |

(Continued)

OTHER PUBLICATIONS

Non-Final Office Action received for U.S. Appl. No. 14/032,435, dated Apr. 3, 2015, 9 Pages.

*Primary Examiner* — Hiep V Nguyen
(74) *Attorney, Agent, or Firm* — Shook, Hardy & Bacon, L.L.P.

(57) ABSTRACT

A system transfers healthcare session operation data between a portable device and a first computer. The portable device includes, an imaging device for acquiring image data including a readable code from a displayed image associated with a current operating session of a first application and presented by the first computer. A code interpreter for image to text conversion converts the readable code to text comprising a URL (universal resource locator) and context data associated with the current operating session. An executable application automatically initiates a session of operation of a second application corresponding to the current operating session of the first application, on the portable device in response to the text. A display processor generates data representing at least one display image associated with the session of operation of the second application.

20 Claims, 11 Drawing Sheets

(56) References Cited

U.S. PATENT DOCUMENTS

| | | |
|---|---|---|
| 2004/0172300 A1 | 9/2004 | Mihai et al. |
| 2005/0057436 A1* | 3/2005 | Alden .................. G06F 19/327 345/2.1 |
| 2005/0101844 A1 | 5/2005 | Duckert et al. |
| 2005/0277872 A1* | 12/2005 | Colby et al. .................... 604/67 |
| 2006/0106648 A1* | 5/2006 | Esham et al. ..................... 705/3 |
| 2008/0011825 A1 | 1/2008 | Giordano et al. |
| 2008/0017722 A1 | 1/2008 | Snyder et al. |
| 2008/0028214 A1 | 1/2008 | Tafoya et al. |
| 2008/0189170 A1 | 8/2008 | Ramachandra |
| 2008/0198028 A1 | 8/2008 | Watanabe |
| 2008/0261526 A1 | 10/2008 | Suresh |
| 2009/0037515 A1 | 2/2009 | Zapata et al. |
| 2009/0112072 A1 | 4/2009 | Banet et al. |
| 2010/0001838 A1 | 1/2010 | Miodownik et al. |
| 2010/0012715 A1 | 1/2010 | Williams et al. |
| 2010/0038417 A1 | 2/2010 | Blankitny |
| 2010/0065634 A1 | 3/2010 | Nakamura |
| 2010/0169120 A1 | 7/2010 | Herbst et al. |
| 2010/0169121 A1 | 7/2010 | Herbst et al. |
| 2010/0219242 A1 | 9/2010 | Gangi |
| 2010/0230485 A1 | 9/2010 | Kenney |
| 2010/0271208 A1 | 10/2010 | Steinmetz et al. |
| 2011/0072263 A1 | 3/2011 | Bishop et al. |
| 2011/0081860 A1 | 4/2011 | Brown et al. |
| 2011/0101115 A1 | 5/2011 | Rampersad |
| 2011/0125521 A1* | 5/2011 | Dhoble ............................ 705/2 |
| 2011/0131061 A1 | 6/2011 | Shain |
| 2011/0210170 A1 | 9/2011 | Arguello |
| 2011/0297747 A1 | 12/2011 | Naumovsky |
| 2011/0302051 A1 | 12/2011 | Arbatti |
| 2011/0313870 A1 | 12/2011 | Eicher et al. |
| 2012/0029303 A1* | 2/2012 | Shaya ........................... 600/300 |
| 2012/0041782 A1 | 2/2012 | Morris |
| 2012/0072536 A1 | 3/2012 | Xu et al. |
| 2012/0179908 A1* | 7/2012 | Duma .......................... 713/165 |
| 2012/0205441 A1 | 8/2012 | Utech et al. |
| 2013/0013548 A1 | 1/2013 | Alexander et al. |
| 2013/0098983 A1 | 4/2013 | Neff |
| 2013/0128305 A1* | 5/2013 | Grabkowitz et al. ......... 358/1.15 |
| 2013/0185092 A1 | 7/2013 | Dubbels et al. |
| 2014/0067426 A1 | 3/2014 | Neff |
| 2014/0288947 A1 | 9/2014 | Simpson et al. |
| 2014/0351175 A1 | 11/2014 | Venkat et al. |

\* cited by examiner

Figure 3

| Session ID | Current Software Module | Current Software Module address | Unsaved form entry data |
|---|---|---|---|
| ABCDEFG1234567890 | Order Entry | orderentry.jsp | formid=1, formitem=2, value="heavy breathing" |
| HIJKLMNO1234567890 | Results | results.jsp | |

Figure 4

| Desktop Module | Mobile Equivalent | Form Mappings (format: FORMID-FORMITEM:MOBILEFORMID-MOBILEFORMITEM) | Sample |
|---|---|---|---|
| orderentry.jsp | mobileorderentry.jsp | 1-2:1-1 | Maps Value of "heavy breathing" entered in from formid=1, formitem=2 on the desktop to formid=1, formitem=1 on the mobile device |
| results.jsp | mobileresults.jsp | | |

403   406   409   412

Figure 11
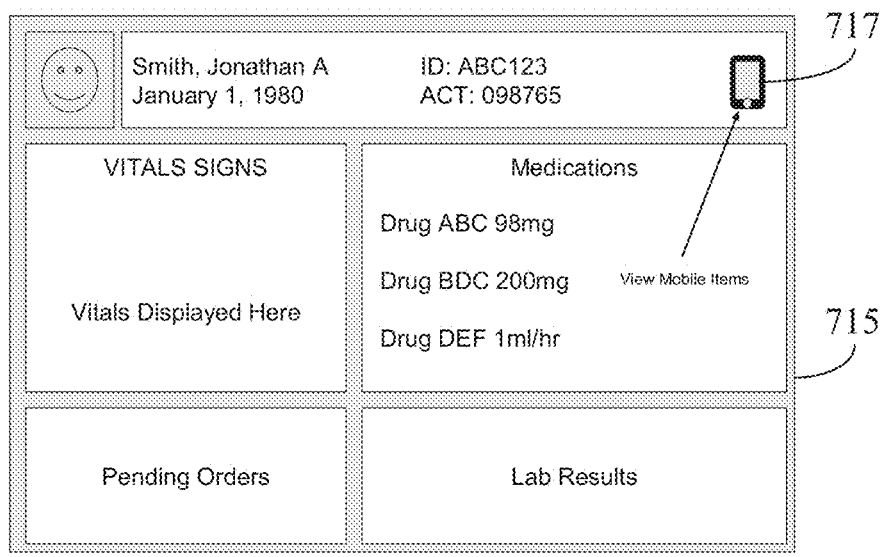
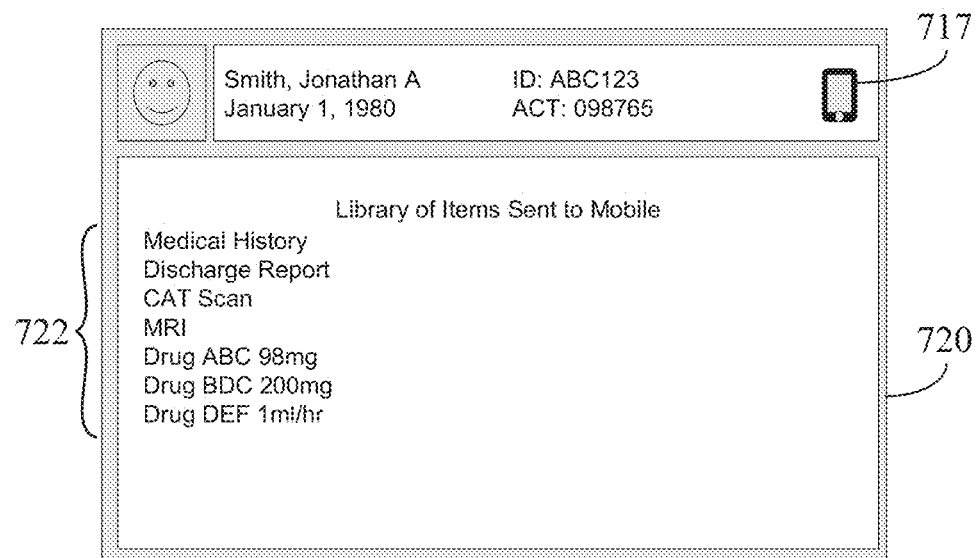
Figure 12

HEALTHCARE INFORMATION OPERATION SESSION AND DATA TRANSFER SYSTEM

This is a non-provisional application of provisional application Ser. No. 61/706,300 filed Sep. 27, 2012, by R. Neff.

FIELD OF THE INVENTION

This invention concerns a healthcare information system for transferring healthcare session operation data between a portable processing device and a first computer in response to text derived from image data representing a readable code.

BACKGROUND OF THE INVENTION

Mobile devices are becoming more common in healthcare and other settings and there is a widespread need to utilize these devices for performing the tasks of non-portable computers. However, due to the relative difficulty of entering data and commands into portable (mobile) devices through lack of physical keyboards, portable devices are largely used for processing available and already entered information rather than for entering it. Further known healthcare information systems lack a capability to readily transfer session operation data between a computer and a portable processing device dependent on a type of task being performed. A system according to invention principles addresses these deficiencies and related problems.

SUMMARY OF THE INVENTION

A system employs QR (quick response) codes, bar codes, and other visually coded identifiers, to transfer a computer operation session and data between a computer and a portable device, for example and to provide other direct and indirect communication links to a session and to data. A healthcare information system transfers healthcare session operation data between a portable processing device and a first computer. The portable processing device includes, an imaging device for acquiring image data including a readable code from a displayed image associated with a current operating session of a first healthcare information processing application and presented by the first computer. A code interpreter for image to text conversion converts the readable code to text comprising a URL (universal resource locator) and context data associated with the current operating session. An executable application automatically initiates a session of operation of a second healthcare information application corresponding to the current operating session of the first healthcare information processing application, on the portable processing device in response to the text. A display processor generates data representing at least one display image associated with the session of operation of the second healthcare information system application.

BRIEF DESCRIPTION OF THE DRAWING

FIG. 3 shows a lookup table associating a session identifier with an executable application and an executable application address and with entered data, according to an embodiment of the invention.

FIG. 4 shows a lookup table associating a computer executable application with a mobile version of the application and form data mapping information for mapping form data between a desktop application form and a mobile version of the form, according to an embodiment of the invention.

FIG. 11 shows a display image presenting a selectable icon on a portable processing device for initiating presentation of transferred information items, according to an embodiment of the invention.

FIG. 12 shows a display image presenting transferred information items, according to an embodiment of the invention.

DETAILED DESCRIPTION OF THE INVENTION

A system employs QR (quick response) codes, bar codes, and other visually coded identifiers, to transfer computer operation sessions and provide other direct and indirect communication links to a session and to data. The links support communication between a computer (e.g. a non-portable computer, laptop, notebook, tablet or smartphone, for example) and a portable device (computer, laptop, notebook, tablet or smartphone, for example), for example.

Figure 1:
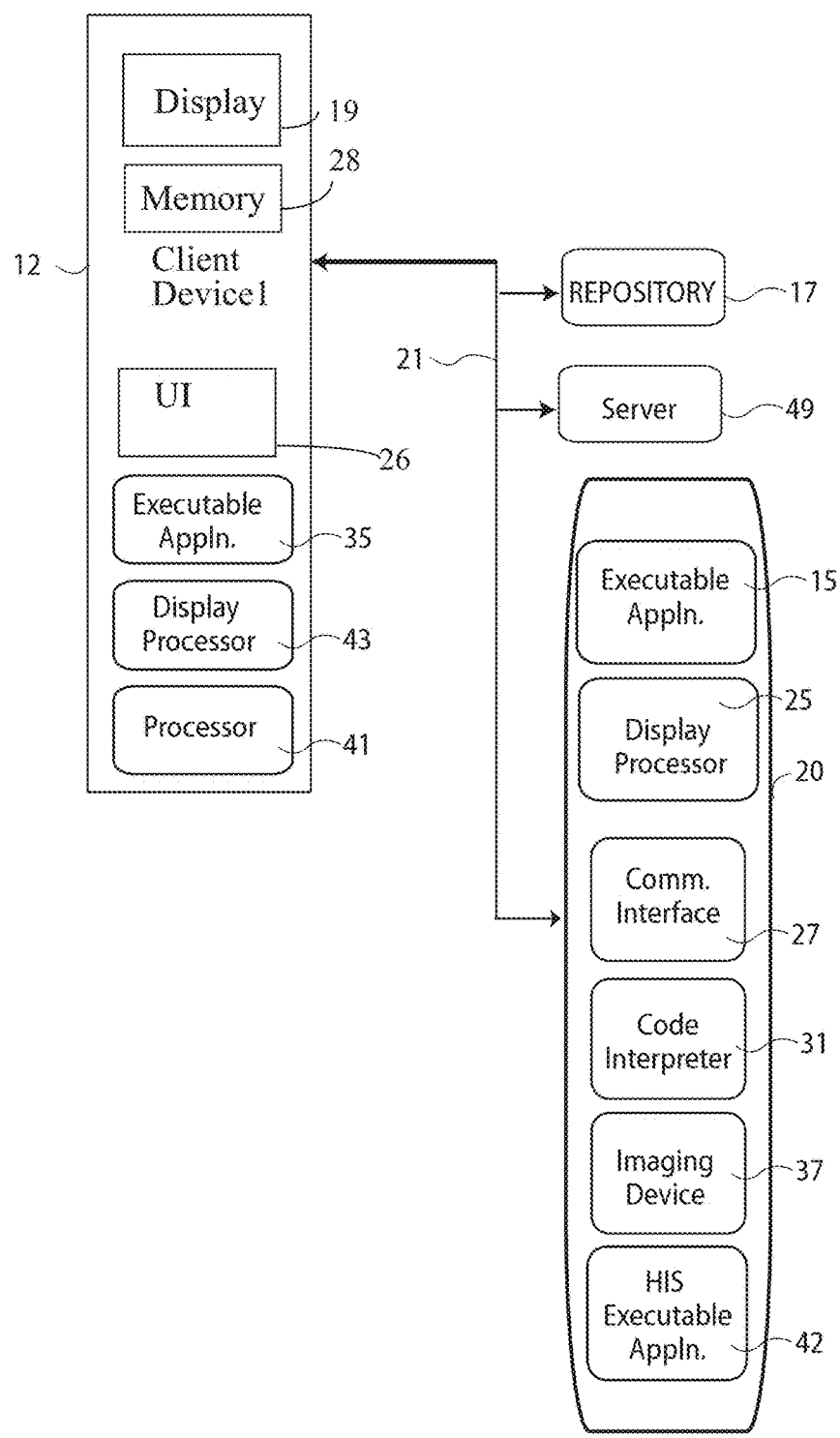
FIG. 1 shows a healthcare information system for transferring healthcare session operation data between a portable processing device and a first computer, according to an embodiment of the invention.

FIG. 1 shows healthcare information system 10 for transferring healthcare session operation data between portable processing device 20 and first computer 12. System 10 includes computer 12, portable processing device 20, at least one repository 17 and server 49. Computer 12 operates in conjunction with server 49 and bidirectionally communicates with portable processing device 20 via network 21. Computer 12 includes memory 28, a user interface 26 enabling user interaction with a Graphical User Interface (GUI) and display 19 supporting GUI and medical data, image and administrative information presentation in response to predetermined user (e.g., physician, nurse administrator) specific preferences. At least one repository 17 stores readable codes (e.g. quick response (QR), bar and other codes) representing URLs (universal resource locators) in association with context data and with a current operating session of an executable application and a current operating context of the executable application and with an image provided by the executable application. Repository 17 also stores particular application context data including a patient identifier, a user identifier, a session identifier, a patient name and a patient visit identifier.

Portable processing device 20 includes imaging device 37 for acquiring image data including a readable code from a displayed image associated with a current operating session of a first healthcare information processing application 35 and presented on display 19 of computer 12. Code interpreter 31 provides image to text conversion and converts the readable code to text comprising a URL (universal resource locator) and context data associated with the current operating session. Executable application 15 automatically initiates a session of operation on device 20 of a second healthcare information system application 42 corresponding to the current operating session of the first healthcare information processing application 35, in response to the text. Display processor 25 generates data representing at least one display image associated with the session of operation of second healthcare information system application 42. In one embodiment, code interpreter 31 converts a second readable code to data initiating communication of a message by communication interface 27 that initiates a session of operation of a third healthcare information system application (not shown) on computer 12. The third healthcare information system application corresponds to a current operating session of second healthcare information processing application 42. In one embodiment, the third healthcare information system application comprises an instance of the first healthcare information processing application 35.

Computer 12 includes executable application 35, processor 41 and display processor 43. Executable application 35 performs multiple patient data related functions and displays multiple display images associated with the multiple functions. Processor 41 dynamically generates a readable code representing text comprising a URL (universal resource locator) and context data associated with a current operating session of the executable application and incorporates the generated readable code in data representing a display image associated with a function and the current operating context of executable application 35. Display processor 43 generates data representing the display image for presentation on display 19 of computer 12.

Figure 2:
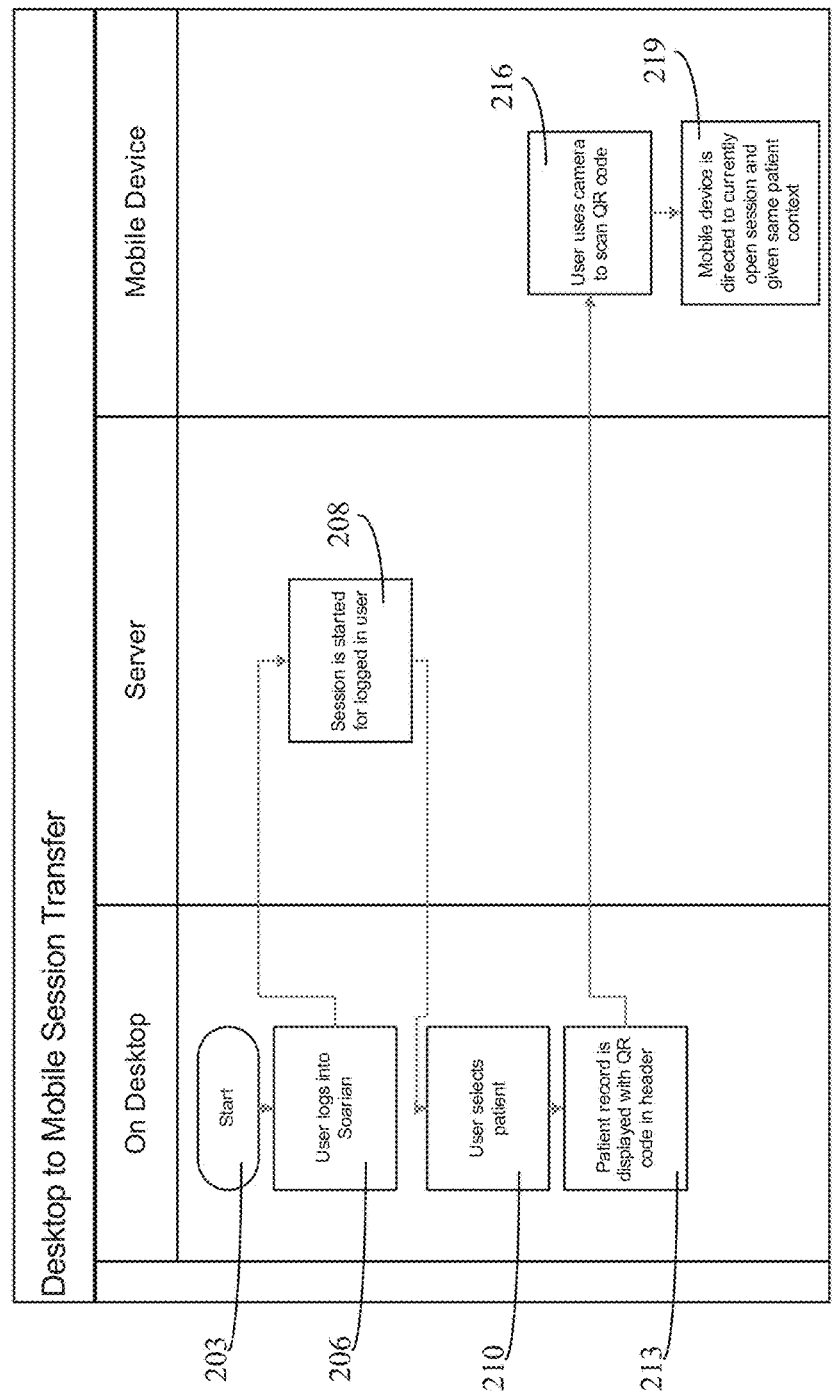
FIG. 2 shows a flowchart of a process for computer to portable processing device session transfer, according to an embodiment of the invention.
Figure 7:
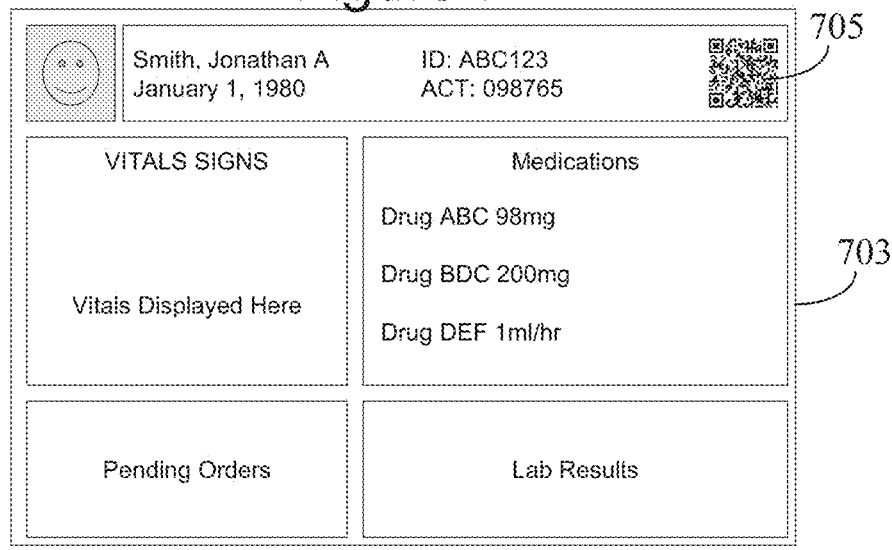
FIG. 7 shows a display image with a readable QR code, according to an embodiment of the invention.

FIG. 2 shows a flowchart of a process for session transfer from computer 12 (FIG. 1) to portable processing device 20. In step 206, following the start at step 203, a user logs into computer 12 and initiates a session of computer operation via server 49 in step 208. The user selects and accesses data of a particular patient using executable application 35 executing on computer 12 in step 210 and displays the patient data in image 703 on display 19 in step 213. FIG. 7 shows display image 703 with readable QR code 705 on display 19 of computer 12. Readable QR code 705 represents a URL. A user in step 216 scans QR code 705 in the patient context header on the upper right hand side of displayed image 703 with imaging device 37 on portable processing device 20. Imaging device 37 may be a camera, bar code scanner, or other reading device.

In response, device 20 accesses the URL in step 219 and a browser on device 20 is directed to a web page presenting the particular patient data and context information corresponding to the data of the particular patient presented by computer 12 using executable application 35. Thereby, the computer 12 session is transferred to portable device 20 which displays the same user session and data of the selected patient previously presented as the computer 12 operation session. The user does not need to log in again on portable processing device 20 or select the patient, reducing transfer time and facilitating user friendly operation of the system. In another embodiment, the system initiates an equivalent application and display image presentation on portable processing device 20. For example, if a user employs an order entry image presented on display 19 of computer 12, the system transfers the user to an equivalent order entry display image on a portable tablet. If this is not feasible, the system transfers a user to the most detailed relevant page to retain as much context compatibility between computer 12 and portable processing device 20 as possible. Consequently, as a result of session transfer, a user of portable processing device 20, (i) becomes logged in on the same order entry page for a particular patient as presented on display 19 of computer 12, (ii) becomes logged in with the particular patient selected but without the same order entry page for the particular patient being displayed or (iii) becomes logged in without any particular patient data being displayed. In another embodiment, at least one of applications 15, 35 and 42 execute on server 49.

System 10 (FIG. 1) advantageously uses a QR (or other) code to transfer a clinical executable application computing session between two different device platforms (including mobile, desktop, tablet, smartphone platforms, for example) bringing a user to the most relevant spot in the clinical executable application on a different platform with as much clinical context retained as possible. Clinical context includes data identifying, a logged in user, a selected patient, a selected hospital entity, a selected patient visit and an executable application image and function, for example. In response to use of imaging device 37 on portable processing device 20 to scan a QR code on a computer 12 display image, a web browser (or custom application) of portable processing device 20 is directed to the corresponding or same session that is currently open, but the mobile version of that same displayed page.

In an operation example, a hospital information system (HIS) executable application presents a QR code on a display image on display 19 of computer 12. The QR code comprises a link to a mobile version of the corresponding current image on display 19 and associated computer operation session. The link includes a type of (optionally encrypted) key (for example: http://mobile.clinicalsystem.org/orderentry.html?session=ABCDEFG1234567890) where ABCDEFG1234567890 represents clinical context characteristics and data of the session. An example of the URL can be seen above. Information included in the session key in the URL may include, but is not limited to, Patient Name, Patient identifier, session identifier, user identifier, Patient Visit identifier and executable application identifier (such as for an order entry, pharmacy, laboratory test result, admission, discharge, transfer application, for example). Additional information (including partially entered data) included in the session key is found in a lookup table as illustrated in FIG. 3. Specifically, FIG. 3 shows a lookup table associating a session identifier (column 303) with an executable application (column 306) and an executable application address (column 309) and with entered but unsaved form data (column 312). The lookup table may also associate a session identifier with an application identifier, and UI image identifier and application code portion identifier and particular point within an application code portion indicating point in application code portion and associated entered data.

A User employs imaging device 37 on portable processing device 20 to scan the QR code. In response to reading the QR code, a browser (or other application) on device 20 is directed to the website of the link using the user session key to automatically continue the current session open on computer 12. FIG. 4 shows a lookup table associating a computer executable application (column 403) with a mobile version of the application (column 406) and form data mapping information (column 409) for mapping form data between a desktop application form and a mobile version of the form and form data to be mapped (column 412). The lookup table is used to manage links between mobile and desktop versions of executable applications. In another embodiment the mobile device application is the same as the desktop application. The QR code comprises a URL that directs the browser on portable processing device 20 to an operational point of executable application 35 in an already existing session on computer 12 following an authorization verification i.e. login by a user into computer 12 or device 20 and validation of credentials. In one embodiment, the device 20 session concurrently exists with the computer 12 session in another embodiment the computer 12 session is closed and transferred to device 20.

Figure 5:
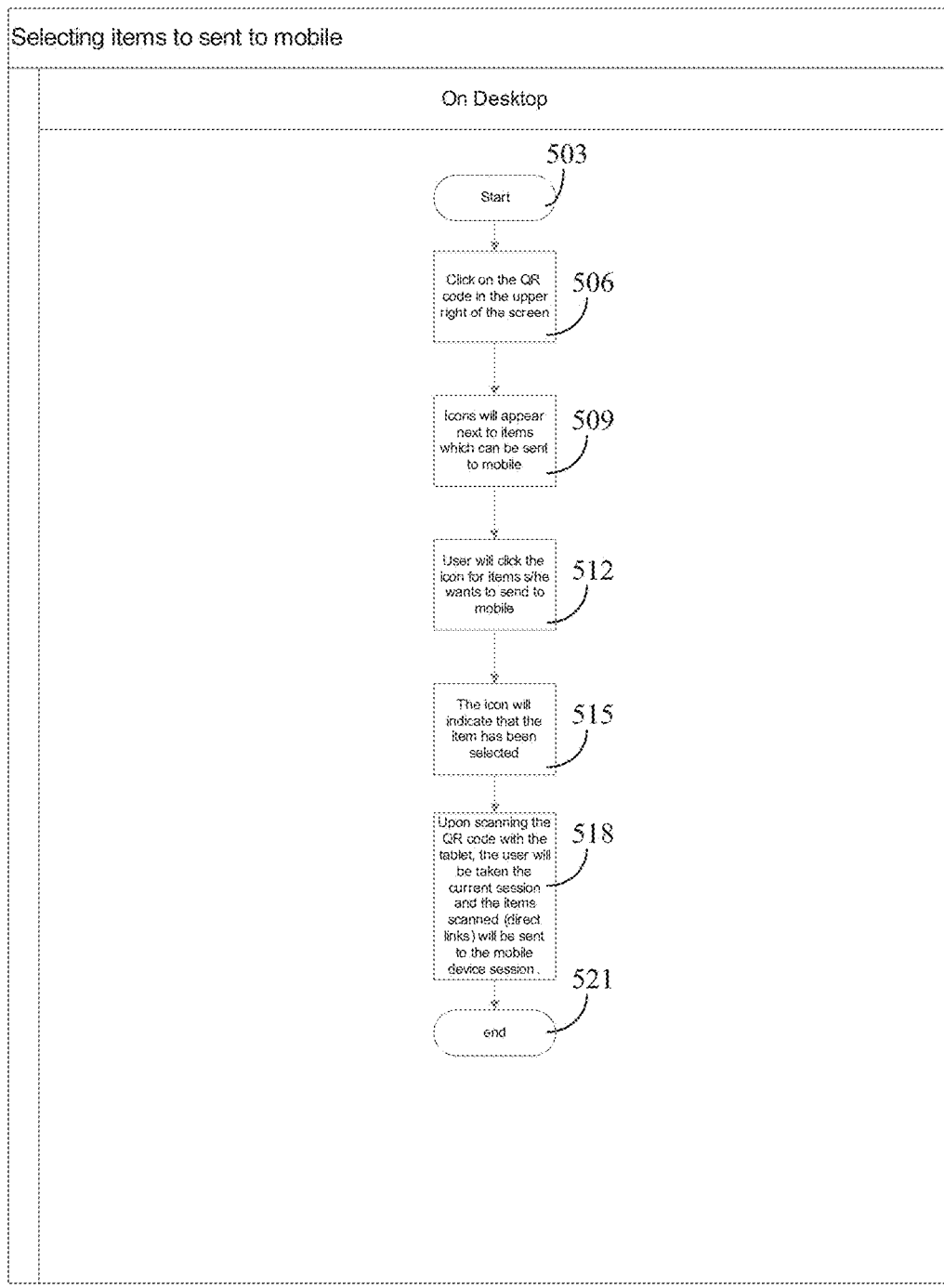
FIG. 5 shows a flowchart of a process for selecting data items on a computer to be sent to a portable processing device, according to an embodiment of the invention.

FIG. 5 shows a flowchart of a process performed by system 10 for selecting data items via an image on display 19 of computer 12 to be sent to portable processing device 20. A clinician may need to use a mobile device to show data, results or images to a patient. These items are often "buried" within an HIS (Healthcare Information System) and require multiple navigational steps and complex navigational paths for access. The system advantageously enables a clinician reviewing a patient record on a desktop computer to share information items with that patient using a direct link to send the information to a patient portable device or other device. The physician is able, using a mobile device, with one click, to access the items and links and share them with a patient. The system thereby provides an easy access list as well as a "to do" and reminder list of information items the clinician wants to share with the patient.

Figure 8:
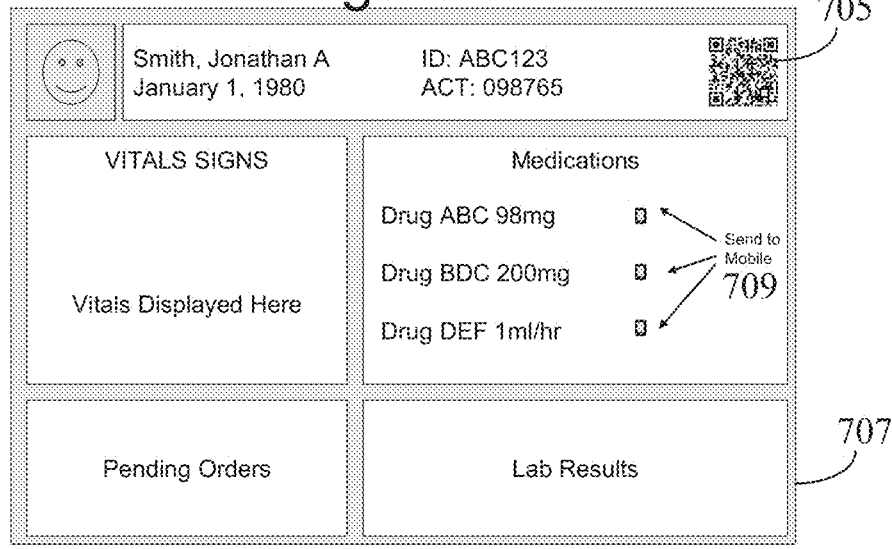
FIG. 8 shows a display image presenting selectable icons for identifying information items to be shared, according to an embodiment of the invention.

In step 506, following the start at step 503, a user selects QR code 705 in the patient context header on the upper right hand side of displayed image 703 on display 19 of computer 12. In step 509 in response to the selection, icons 709 (FIG. 8) are displayed next to each information item which is available to be sent to portable processing device 20. FIG. 8 shows display image 707 presenting selectable icons 709 for identifying information items to be shared. In response to a user in step 512 selecting one or more icons 709 to be shared, a selected icon visually changes in step 515 (by color, shading, highlighting or shape, for example) to signify that it has been selected (it may also be de-selected through the same process). In step 518, in response to a user scanning QR code 705 with imaging device 37, device 20 is directed to a session corresponding to the current session operating on computer 12 incorporating information items 709. Particular patient data and context information items, for example, corresponding to the data of the particular patient presented by computer 12 is transferred to portable device 20 which displays the same user session and data of the selected patient previously presented as the computer 12 operation session. In response to a user selecting QR code 705 again, computer 12 turns off the "Send to mobile" icons, but the selections are stored.

Figure 9:
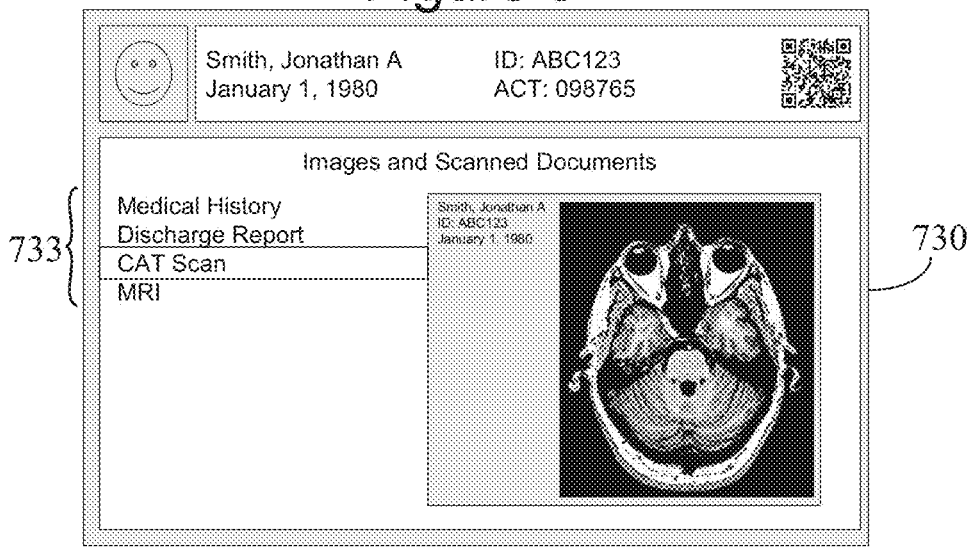
FIGS. 9 and 10 show display images presenting information items to be shared, according to an embodiment of the invention.
Figure 10:
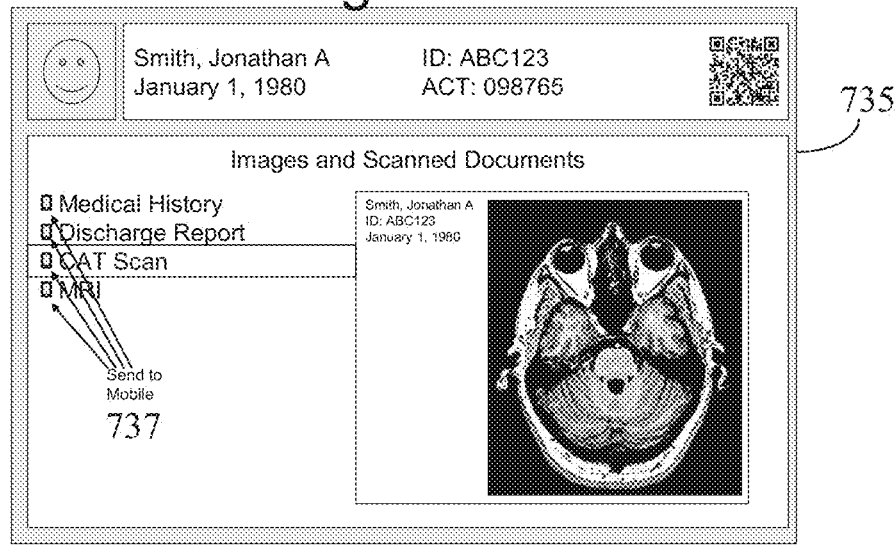

FIG. 11 shows display image 715 on portable processing device 20 presenting selectable icon 717 for initiating presentation of transferred information items. The transferred information items are presented in image 720 (FIG. 12) on device 20 in response to user selection of icon 717. FIG. 12 shows display image 720 presenting transferred information items 722. In response to a user selecting (e.g. clicking on) an individual item of items 722, detailed information of the respective selected item are presented on device 12. FIGS. 9 and 10 show display images on display 19 presenting information items to be shared. FIG. 9 shows information items 733 in image 730 that are sharable with device 20, for example. FIG. 10 shows the information items with selectable icons 737 in image 735 enabling a user to select or exclude individual items for sharing. The process of FIG. 5 terminates in step 521.

Figure 6:
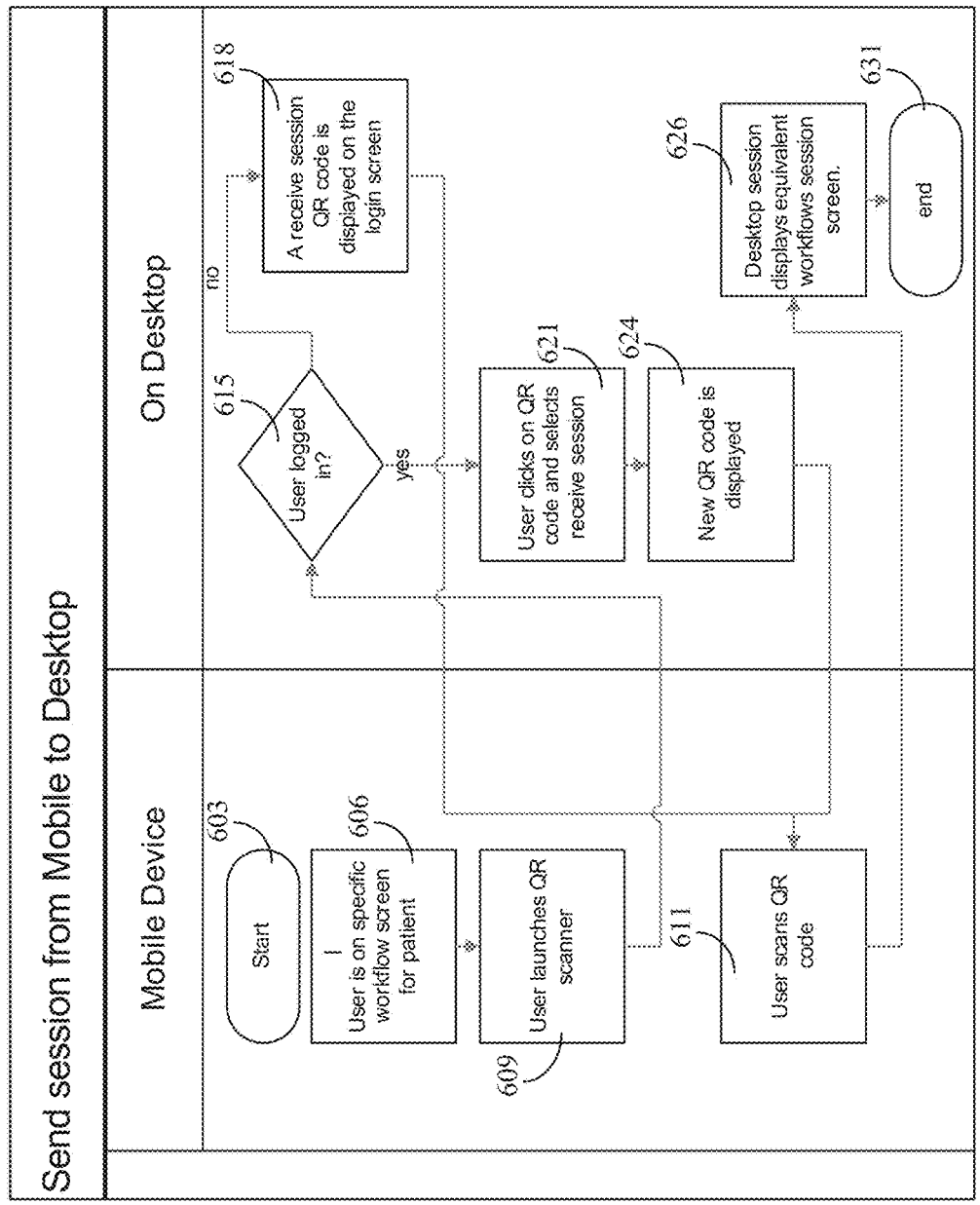
FIG. 6 shows a flowchart of a process for portable processing device to computer session transfer, according to an embodiment of the invention.

FIG. 6 shows a flowchart of a process for session transfer from portable processing device 20 to computer 12. A user in step 606 interacts with a specific workflow related image of executable application 15 presented on portable device 20, following the start at step 603. In step 609 imaging device 37 and its related executable application are activated. If a user is logged in to computer 12 as determined in step 615, the user in step 621 selects a QR code on display 19 and selects a receive session command. In response, in step 624 a new QR code is displayed on an image on display 19 of computer 12 and a user scans the QR code in step 611 using imaging device 37 on portable device 12. In step 626, in response to the scanning of the QR code, the specific workflow related image of executable application 15 and associated session on portable device 20, is transferred to computer 12 and the process terminates at step 631.

If a user is not logged in to computer 12 as determined in step 615, a receive session QR code is presented on a login image on display 19 on computer 12 in step 618. A user scans the QR code in step 611 using imaging device 37 on portable device 12. In step 626, in response to scanning, the specific workflow related image of executable application 15 and associated session on portable device 20, is transferred to computer 12 and the process terminates at step 631.

If a user of portable processing device 20 needs to perform a task which cannot be easily performed on device 20, the user scans a QR code on the login screen of a desktop computer, or selects the currently displayed QR code (if the system is already logged in) and changes it to a "receive session" QR code. The user scans the QR barcode with the mobile device, which sends a message to the desktop computer which has just been scanned (each desktop computer would display a unique QR code) to log the desktop computer in with the proper user, patient and workflow context which is current on the mobile screen. Example. A user is ready to enter an order on the mobile device, but needs the more functional order entry screen of computer 12. The user transfers the session to the computer 12 (and jumps right to the order entry screen for that patient) and enters the order without needing to login, select a patient or navigate to the order entry screen.

Figure 13:
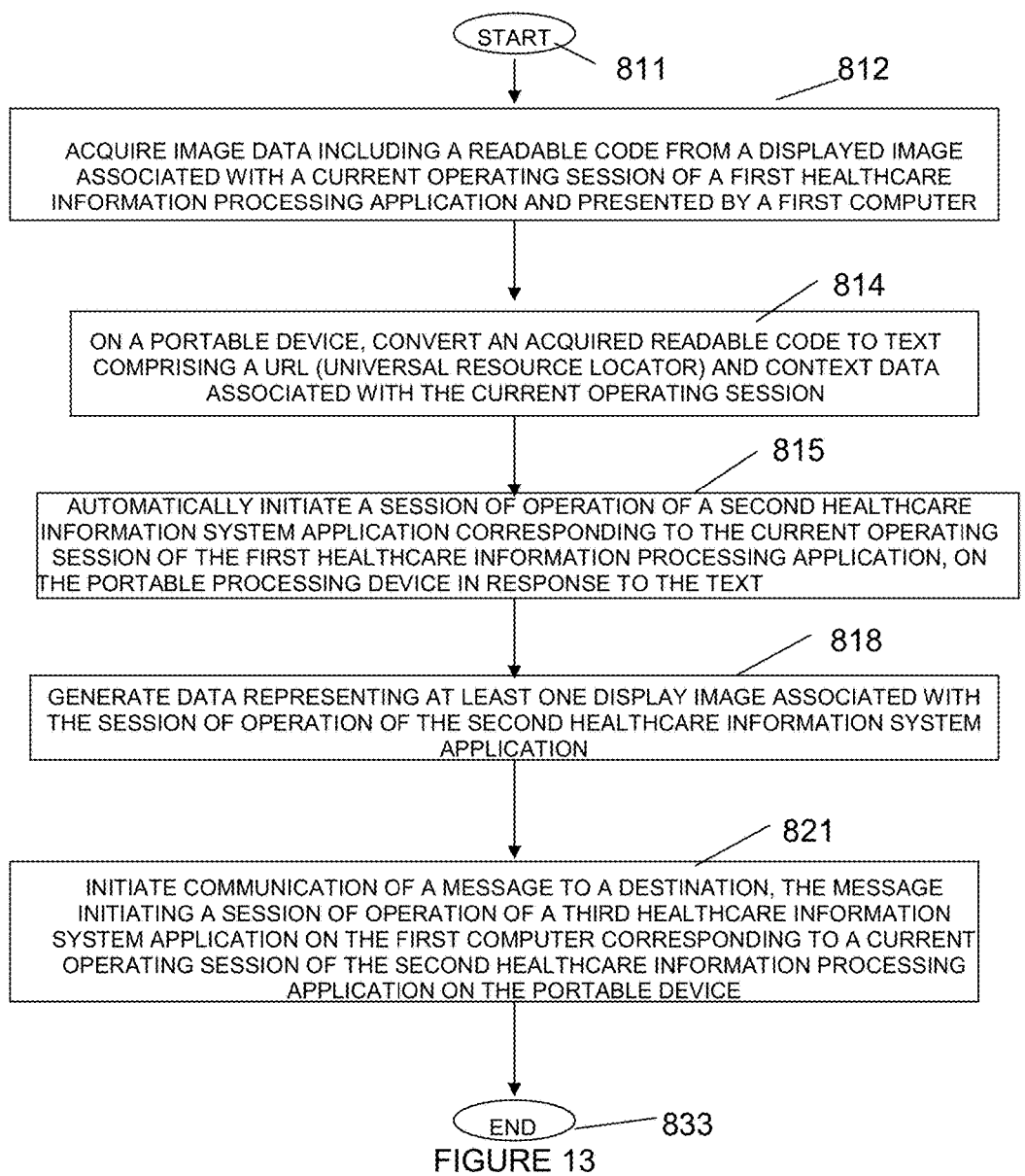
FIG. 13 shows a flowchart of a process performed by a portable processing device for transferring healthcare session operation data between the portable processing device and a computer, according to an embodiment of the invention.

FIG. 13 shows a flowchart of a process performed by a portable processing device 20 and system 10 (FIG. 1) for transferring healthcare session operation data between portable processing device 20 and computer 12. Computer 12 comprises at least one of, (a) a non-portable computer, (b) a laptop computer, (c) a notebook computer, (d) a smartphone and (e) a tablet computer. In step 812 following the start at step 811, imaging device 37 in portable processing device 20 acquires image data including a readable code from a displayed image associated with a current operating session of first healthcare information processing application 35 and presented by computer 12. The readable code comprises at least one of, (a) a QR (Quick Response) code and (b) a bar code. Code interpreter 31 for image to text conversion in step 814 converts the readable code to text comprising a URL (universal resource locator) and context data associated with the current operating session. The context data comprises particular application context data including at least two of, (a) a patient identifier, (b) a user identifier, (c) a session identifier, (d) a patient name, (e) a patient visit, (f) an identifier of a particular application displayed image and (g) an application function identifier, presented in at least one display image. In step 815 executable application 15 on portable processing device 20 in response to the text, automatically initiates a session of operation of second healthcare information system application 42 corresponding to the current operating session of the first healthcare information processing application 35.

Second healthcare information system application 42 comprises a mobile executable application providing reduced processing burden relative to corresponding non-mobile first healthcare information processing application 35. Second healthcare information system application 42 comprises at least one of, (a) an order entry application, (b) a pharmacy application, (c) an admission, discharge and transfer application, (d) a patient data and laboratory test result application and (e) a patient administration application. In one embodiment, first healthcare information processing application 35 and second healthcare information system application 42 are substantially the same application or are different operational instances of substantially the same application. Executable application 15 selects second healthcare information system application 42 using predetermined information associating mobile executable application 42 with the non-mobile first healthcare information processing application 35. Executable application 15 automatically initiates the session of operation of second healthcare information system application 42 with substantially the same context as the corresponding current operating session of first healthcare information processing application 35 in response to the context data.

Display processor 25 in step 818 generates data representing at least one display image associated with the session of operation of second healthcare information system application 42. In step 821, imaging device 37 acquires image data including a second readable code from a displayed image. Code interpreter 31 converts the second readable code to data initiating communication of a message by communication interface 27. The message initiates a session of operation of a third healthcare information system application on computer 12 corresponding to a current operating session of second healthcare information processing application 42. In one embodiment, the readable code indicates information items accessible by portable processing device 20 comprising a list of user selectable items. In response to user command, portable processing device 20 acquires and displays the selected information items. The process of FIG. 13 terminates at step 833.

Figure 14:
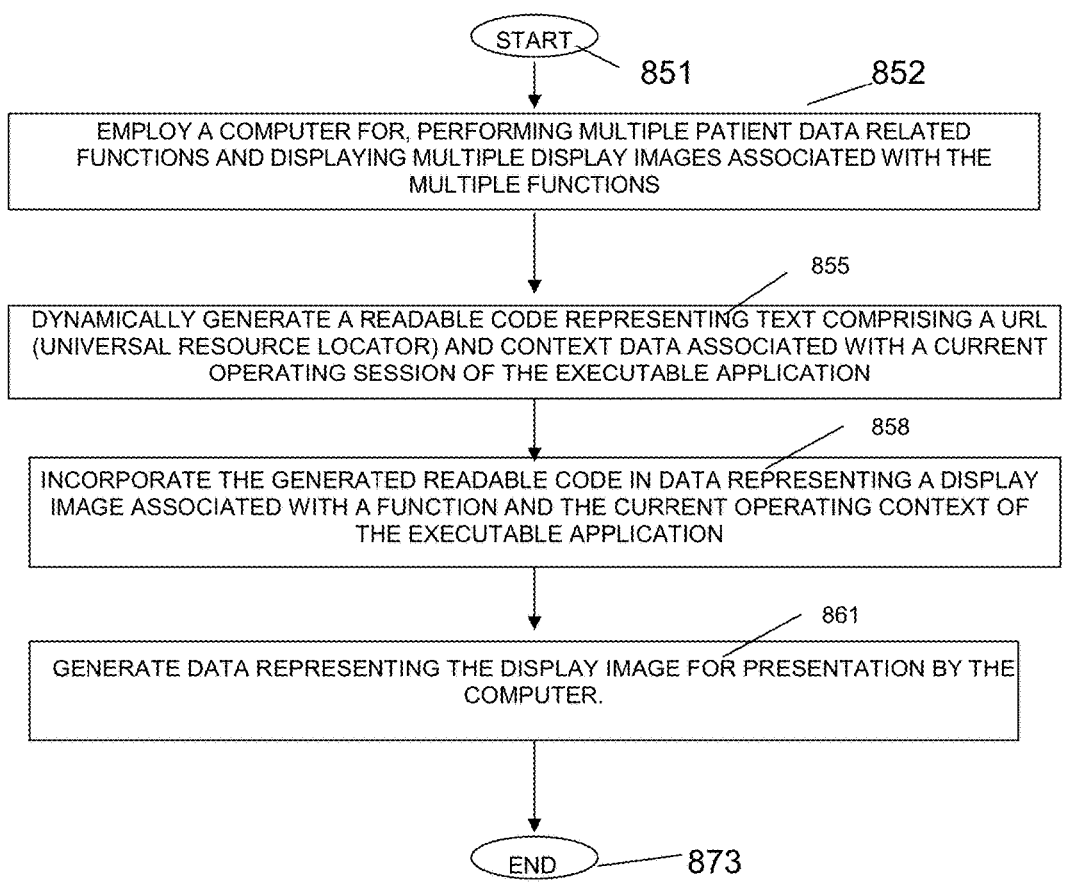
FIG. 14 shows a flowchart of a process performed by a healthcare information system computer for transferring healthcare session operation data between a portable processing device and the computer, according to an embodiment of the invention.

FIG. 14 shows a flowchart of a process performed by healthcare information system computer 12 and system 10 (FIG. 1) for transferring healthcare session operation data between portable processing device 20 and the computer. In step 852 following the start at step 851, executable application 35 of computer 12, performs multiple patient data related functions and displays multiple display images associated with the multiple functions. Processor 41 in step 855, dynamically generates a readable code representing text comprising a URL (universal resource locator) and context data associated with a current operating session of executable application 35. In step 858, processor 41 incorporates the generated readable code in data representing a display image associated with a function and the current operating context of executable application 35. Display processor 43 in step 861, generates data representing the display image for presentation by computer 12. In response to device 20 scanning a code displayed in the display image, a computer 12 operation session is transferred to device 20 as a concurrently open session. The process of FIG. 14 terminates at step 873.

A computer as used herein may comprise a portable computer such as a laptop, notebook, smartphone, tablet, for example as well as a non-portable computer. A session may be transferred from a smart phone to a tablet, for example, and a session on one computer may be replicated (not transferred) to another device. Thereby if two doctors are standing next to each other, one doctor may acquire patient context from the other if the second doctor is logged into the system. This embodiment comprises context transfer rather than session transfer. In one embodiment, in response to a mobile device scanning a code on the desktop, the mobile device issues a command to the server serving the desktop session requesting the server to switch the desktop session to the session which is currently open on the mobile device.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-14 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system employs QR codes, bar codes, and other visually coded identifiers, to transfer computer operation sessions and provide other direct and indirect communication links to a session and to data. Further, the processes and applications may, in alternative embodiments, be located on one or more (e.g., distributed) processing devices on a network linking the units of FIG. 1. Any of the functions and steps provided in FIGS. 1-14 may be implemented in hardware, software or a combination of both. No claim element herein is to be construed under the provisions of 35 U.S.C. 112, sixth paragraph, unless the element is expressly recited using the phrase "means for."

What is claimed is:

1. A healthcare information system for transferring healthcare session operation data between a portable processing device and a first computer, comprising:
   a non-portable computing device including,
   a first healthcare information processing application having context data associated with a current operating session, wherein the context data includes a current application module within the first healthcare information processing application, and an application code portion identifier indicating a point in the first healthcare information processing application corresponding to the current operating session;
   at least one processor for generating a readable code corresponding to the context data associated with the current operating session;
   a display processor for generating a first display image representing the readable code; and
   a display for presenting the first display image;
   a lookup table comprising a mapping of the context data for the current operating session of the first healthcare information processing application to equivalent mobile operating sessions for one or more mobile versions of the first healthcare information processing application, the equivalent mobile operating sessions comprising locations within the one or more mobile versions equivalent to the application code portion identifier, and
   a portable processing device including,
   an imaging device for acquiring the first display image;
   a code interpreter for reading the readable code from the acquired first display image;
   a mobile executable application for automatically initiating a mobile instance of the current operating session, in response to the reading the readable code from the acquired first display image, wherein,
   the mobile executable application is a mobile version of the one or more mobile versions of the first healthcare information processing application; and
   the mobile executable application initiates the mobile instance of the current operating session, according to the lookup table, at an equivalent location within the mobile executable application corresponding to the application code portion identifier in the first healthcare information processing application;
   a display processor for generating a graphical user interface for user interaction with the mobile instance of the mobile instance of the current operating session; and
   a portable processing device display for presenting the graphical user interface.

2. A system according to claim 1, wherein the mobile executable application is configured to initiate the mobile instance of the current operating session including a second display image corresponding to the first healthcare information processing application.

3. A system according to claim 2, wherein the first healthcare information processing application is a non-mobile application and the portable processing device selects the mobile executable application using predetermined information in the lookup table associating the mobile executable application with the non-mobile first healthcare information processing application.

4. A system according to claim 1, wherein the first healthcare information processing application and the mobile executable application are the same application.

5. A system according to claim 4, wherein the first healthcare information processing application and the mobile executable application are different operational instances of the same application.

6. A system according to claim 1, wherein the readable code comprises an encryption key.

7. A system according to claim 1, wherein the executable application automatically initiates the mobile instance of the current operating session with the same context as the current operating session of the first healthcare information processing application in response to the context data, the context comprising a particular application displayed image and an application function.

8. A system according to claim 7, wherein the context data comprises particular application context data including at least two of, (a) a patient identifier, (b) a user identifier and (c) a session identifier, and the at least one display image presents the context data.

9. A system according to claim 7, wherein the context data comprises particular application context data including at least one of, (a) a patient name, and (b) a patient visit identifier.

10. A system according to claim 7, wherein the mobile executable application comprises at least one of, (a) an order entry application, (b) a pharmacy application, (c) an admission, discharge and transfer application, and (d) a patient administration application.

11. A system according to claim 1, wherein the readable code indicates information items accessible by the mobile executable application and the portable processing device.

12. A system according to claim 11, wherein the data indicating information items accessible by the portable processing device comprises a list of user selectable items, and in response to a user command, the portable processing device acquires and displays the selected information items.

13. A system according to claim 1, wherein the non-portable computing device comprises at least one of, (a) a non-portable computer, (b) a laptop computer, and (c) a notebook computer.

14. A system according to claim 1, including a communication interface for initiating communication of a message to a destination, wherein the imaging device acquires image data including a second readable code from a displayed image and the code interpreter converts the second readable code to data initiating communication of a message by the communication interface, the message initiating a session of operation of a third healthcare information application on the non-portable computing device corresponding to a current operating session of the mobile executable application.

15. A healthcare information system for transferring healthcare session operation data between a portable processing device and a computer, comprising:
   a non-portable computer including,
   a first healthcare information processing application having context data associated with a current operating session, wherein the context data includes a current application module within the first healthcare information processing application, and an application code portion identifier indicating a point in the first healthcare information processing application corresponding to the current operating session;
   a non-portable executable application for executing the first healthcare information processing application, wherein executing the first healthcare information processing application comprises performing a plurality of patient data related functions and displaying a plurality of display images associated with said plurality of patient data related functions;
   a processor for, dynamically generating a readable code representing text comprising a URL (universal resource locator) and said context data associated with said current operating session of said non-portable executable application, wherein said readable code comprises a Quick Response (QR) code or a bar code, and incorporating the generated readable code in data representing a said current operating session of said non-portable executable application; and
   a display processor for generating data representing said display image for presentation by said non-portable computer;
   a repository including a lookup table comprising a mapping of the context data for the current operating session of the first healthcare information processing application to equivalent mobile operating sessions for one or more mobile versions of the first healthcare information processing application, the equivalent mobile operating sessions comprising locations within the one or more mobile versions equivalent to the application code portion identifier, and
   a portable processing device including,
   an imaging device for acquiring said data representing said current operating session of said first healthcare information processing application;
   a mobile executable application for automatically initiating a mobile instance of said current operating session, in response to acquiring said data representing said current operating session, wherein;
   said mobile executable application is a mobile version of the non-portable executable application,
   the mobile executable application initiates a mobile instance of said current operating session at a point in said mobile executable application corresponding to said current operating session of said first healthcare information processing application; and
   a display for presenting a graphical user interface for interaction with said mobile instance of said current operating session.

16. A system according to claim 15, wherein said context data comprises particular application context data including at least two of, (a) a patient identifier, (b) a user identifier and (c) a session identifier.

17. A system according to claim 15, wherein said context data comprises particular application context data including at least one of, (a) a patient name and (b) a patient visit identifier.

18. A system according to claim 15, wherein in response to said portable processing device scanning a code displayed in said display image, said current operation session is automatically terminated on said non-portable computer.

19. A method for transferring healthcare session operation data between a portable processing device and a first computer, comprising the activities of:
   employing a portable processing device for,
   acquiring image data including a readable code from a displayed image associated with a current operating session of a first healthcare information processing application and presented by a first computer, wherein the readable code represents a universal resource locator (URL);
   wherein the displayed image represents context data for the current operating session and includes an application code portion identifier indicating a point in the first healthcare information processing application corresponding to the current operating session;
   converting said readable code to text, wherein the text comprises the URL and the context data associated with said current operating session;
   on said portable processing device, in response to converting said readable code to said text, automatically initiating a mobile instance of a session of operation of a second healthcare information application corresponding to said current operating session of said first healthcare information processing application, wherein said second healthcare information application is a mobile version of the first healthcare information application and the second healthcare information application initiates said mobile instance of said current operating session at a point in said second healthcare information processing application corresponding to said current operating session; and
   generating data representing at least one display image associated with said session of operation of said second healthcare information application.

20. One or more non-transitory computer storage media devices having computer-executable instructions embodied thereon for performing a method for transferring healthcare session operation data between a first processing device and a second processing device, the method comprising:
   employing the first processing device for,
   executing a first healthcare information processing application by an executable application, wherein executing the first healthcare information processing application comprises performing a plurality of patient data related functions and displaying a plurality of display images associated with said plurality of functions;

dynamically generating a readable code representing text comprising a URL (universal resource locator) and context data associated with a current operating session of said executable application, wherein the readable code represents a universal resource locator (URL);

associating, with the generated readable code, data representing a said current operating session of said executable application, wherein the data represents context data for the current operating session and includes an application code portion identifier indicating a point in the first healthcare information processing application corresponding to the current operating session;

associating the context data for the current operating session of the first healthcare information processing application with equivalent mobile operating sessions for one or more mobile versions of the first healthcare information processing application; and presenting said readable code including said data representing said context data on a display of said first processing device, wherein said readable code includes instructions to initiate said current operating session on said second processing device upon acquiring said readable code by said second processing device.

* * * * *